United States Patent [19]

Jolles et al.

[11] 4,013,788

[45] Mar. 22, 1977

[54] WATERSOLUBLE EXTRACTS OF CORYNEBACTERIA, PROCESS FOR OBTAINING THEM AND THEIR USE

[75] Inventors: Pierre Jolles, Paris; Daniele Migliore-Samour, Kremlin-Bicetre, both of France

[73] Assignee: Agence Nationale de Valorisation de la Recherche (ANVAR), Neuilly sur Seine, France

[22] Filed: Apr. 30, 1975

[21] Appl. No.: 573,200

[30] Foreign Application Priority Data

May 6, 1974  France .............................. 74.15570

[52] U.S. Cl. .................................. 424/92; 424/88; 424/95; 424/123; 424/177; 424/195
[51] Int. Cl.² .................. A61K 39/02; A61K 39/00
[58] Field of Search .............. 424/88, 95, 123, 177, 424/195, 92

[56] References Cited

FOREIGN PATENTS OR APPLICATIONS 2,189,021  1/1974  France
2,331,144  1/1974  Germany

OTHER PUBLICATIONS

Chemical Abstracts vol. 80: 144339s & 144340k.
Chemical Abstracts vol. 79: 30413k.

*Primary Examiner*—Donald B. Moyer
*Attorney, Agent, or Firm*—Burgess, Dinklage & Sprung

[57] ABSTRACT

Watersoluble extracts of corynebacteria cells are obtained by a process which comprises the steps of subjecting bacterial residues of corynebacteria containing diaminopimelic acid, e.g. *Corynebacterium parvum* cells, to a mild extraction and of isolating the watersoluble extracts so obtained by physico-chemical methods. Said extracts are useful as immunological adjuvants.

7 Claims, No Drawings

WATERSOLUBLE EXTRACTS OF CORYNEBACTERIA, PROCESS FOR OBTAINING THEM AND THEIR USE

The present invention relates to a process for obtaining low-molecular weight watersoluble extracts derived from corynebacteria cells, the thus obtained watersoluble extracts and pharmaceutical compositions containing the same; the invention further relates to the use of such watersoluble extracts as immunological adjuvants.

There has already disclosed a process for isolating from *Corynebacterium parvum* cells materials having immunological properties; one may cite the article of Tâm NGUYEN-DANG and al. [Proceedings Acad. Sc. Paris, t. 276 June 13, 1973]; in this article the immunological materials are obtained by treatment of *Corynebacterium parvum* cells walls with trypsine in presence of solvents or with formol. The thus-obtained materials are injected as an aqueous suspension, that means that these materials are not watersoluble.

It has now been found, and it is this which is the object of the present invention, that starting with corynebacteria cells, by treatments which do not necessitate the use of enzymes, watersoluble products can be obtained which have an adjuvant and non-orthogenous activity.

Watersoluble extracts according to the present invention contain diaminopimelic acid and have a molecular weight between about $1,000 \pm 200$ and $8,000 \pm 200$.

The process of the present invention comprises the steps of subjecting delipidated bacterial residues of corynebacteria cells to a mild extraction and isolating the thus-obtained watersoluble extract. The water soluble extracts are preferably purified by well known purification methods. The watersoluble extracts of the present invention are advantageously handled and stored in powdered state. In the present specification, the term "mild extraction" means homogenization in aqueous medium effecting autolysis of bacterial cells but does not include chemical modifications or extractions.

The mild extraction of cells is carried out by grinding and homogenizing in an aqueous medium, optionally in the presence of a non-ionic detergent, such as e.g. the product known under the trade name "NP-40".

According to the present invention, the extraction is advantageously carried out at a temperature close to 37° C, which is a physiological temperature. The duration of extraction in accordance with the process of the invention is not critical and should be sufficient for extracting a maximum amount of watersoluble substances and for obtaining the aforesaid watersoluble extracts in good yields, said extraction being conducted in a single step or in plurality of successive steps.

In the meaning of the present specification, the corynebacteria used in the process of the invention are corynebacteria containing diaminopimelic acid (DAP).

Certain corynebacteria answering to this general definition contain meso-DAP and arabinogalactan. They are known as optionally anaerobic. An example of such corynebacteria is *C. diphteriae*.

Other corynebacteria in conformity with this definition and suitable herein include LL DAP and no arabinogalactan. They are known as strictly anaerobic. Amongst corynebacteria of this latter type there can be mentioned for example *C. acnes*, *C. parvum*, *C. anaerobium* and *C. granulosum* and the like.

As a relevant bibliographic reference, one may cite the article by Karl Heinz SCHLEIFER and Otto KANDLER, in Bacteriological Reviews Vol. 36 No. 4, Dec. 1972 pages 407–477, where there are included an enumeration of corynebacteria and the properties thereof. The disclosures of said article are included as a reference in the present specification.

Corynebacteria cells, which are especially preferred according to the invention, are cells of *Corynebacterium parvum*.

Corynebacteria cells used the process of the present invention are previously delipidated, in using for instance the method described by A. Aebi et al, Bull. Soc. Chim. Biol., 35, 661 (1953).

The non-ionic detergent, which may be used in the process of the invention, gives the possibility of dissociating lipidic materials bound to the cells and not having been extracted by the delipidation step the use of a detergent thus enables the extraction yield to be improved.

Following mild extraction, the watersoluble extracts are isolated by centrifugation, salting-out, dialysis and lyophilization i.e. freeze-drying.

The salting-out steps are effected on the supernatant layer obtained by centrifugation of the mixture resulting from the mild extraction by means of solutions of an inorganic salt, such as ammonium sulfate, at various concentrations. In order to carry out the salting-out steps, the temperature of the reaction mixture is preferably raised to a value sufficient for effecting a quick dissolving of the used inorganic salt and obtaining the required saturation; thereafter the mixture is kept at a relatively low temperature, preferably of between about 0° and 6° C, during 6 to 24 hours. The removal of insoluble portions is achieved, in accordance with the process of the invention, preferably by centrifugation at a temperature which is of about 0° to 6° C.

The watersoluble extracts of the invention are thereafter obtained in a dry state, e.g. by freeze-drying from solutions resulting from the aforesaid steps, which do not dialyze through a membrane which retains materials having a molecular weight about 1000; it is for instance possible to use a membrane of the type "Diaflo UM 2" (sold by AMICON).

According to a particularly preferred embodiment of the invention, the watersoluble extracts can be further purified and separated into their components by suitable physico-chemical methods, in particular by chromatography on adsorbents, such as DEAE-cellulose, the product known under the name "DEAE Biogel A" or by filtration, e.g. on polyacrylamide gel, using in particular the products known under trade names "Biogel P10", "Biogel P6" or "Biogel P4".

Thus-obtained watersoluble extracts, which constitute a further aspect of the invention, comprise essentially a mixture of variable proportions of watersoluble fragments of the cell wall, if desired in association with non aminated reducing sugars; the amount of watersoluble fragments of the cell wall contained in the extracts of the invention varies as a function of specific conditions for carrying out the invention, including the time of extraction, the number of salting-out steps and of purification steps.

Hydrosoluble fragments of the cell wall consist essentially of a disaccharide-tetrapeptide, a tetrasaccharide-heptapeptide and the dimer, trimer and tetramer of the latter.

The disaccharide-tetrapeptide has the following molecular composition: N-acetylglucosamine (1), N-acetylmuramic acid (1), alanine (2), glutamic acid (1) diaminopimelic acid (1), and the base structure thereof can be represented by the following:

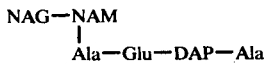

wherein:
NAG = N-acetylglucosamine
NAM = N-acetylmuramic acid
Ala = alanine
Glu = glutamic acid
DAP = diaminopimelic acid.

The tetrasaccharide-heptapeptide has the following molecular composition: N-acetylglucosamine (2), N-acetylmuramic acid (2), alanine (3), glutamic acid (2), diaminopimelic acid (2), and the base structure thereof can be represented by the following:

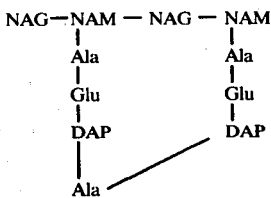

In certain fragments, the acid function or free amine function of DAP may be an substituted by aspartic-acid residue or a glycine residue, which are residues of intercatenary bridges naturally existing within the cell wall.

Non aminated reducing sugars comprise essentially glucose and optionally mannose and galactose.

The composition of thus-obtained watersoluble extracts can be ascertained by conventional methods of determining aminoacid-amino-sugar- and non aminated reducing sugar-contents.

By carrying out the purification step, it is possible to provide by the present invention watersoluble extracts containing mainly tetrasaccharide-heptapeptide, optionally in association with non aminated reducing sugars. Thus, for instance, the watersoluble extracts obtained in a raw state by the process of the invention provide, after chromatography on DEAE-cellulose by means of suitable eluents, a family of substances including disaccharide-tetrapeptide, if desired in association with non aminated reducing sugars and tetrasaccharide-heptapeptide, as well as the dimer, trimer and tetramer thereof, optionally in association with non aminated reducing sugars. In the course of chromatography, the water-soluble materials are isolated in the order of successively decreasing molecular weights.

Since the activity of watersoluble extracts of the invention is linked to the presence of diaminopimelic acid, it is particularly advantageous to isolate, from the raw mixture, materials which are present in sufficient amounts and which have a high content of diaminopimelic acid.

According to one embodiment of the invention, the chromatography is carried out by equilibrating the DEAE-cellulose with a buffer solution having a pH of about 7 and by eluting with an acid buffer having a pH of about 3. It is also possible to separate by chromatography watersoluble extracts containing chiefly tetrasaccharide-heptapeptide possibly in association with non aminated reducing sugars.

The watersoluble extracts obtained in accordance with the invention are endowed with an interesting activity as immunological adjuvants in the absence of any arthrogenous activity.

The adjuvant power is ascertained in the guinea pig, Hartley strains according to the principle of the method of R. G. White et al., Immunology 7, 158 (1964), whereas arthrogenous and protecting powers are ascertained in accordance with methods disclosed by F. Bonhomme, C. R. Acad. Sci. serie D, 263, 1422 (1966) and C. R. Acad. Sci. serie D, 265, 2115 (1967).

In the guinea pig, watersoluble extracts of the invention induce an increase of antibodies level at dosages higher than or equal to 0.1 mg administered intradermally.

The invention also relates to pharmaceutical compositions containing watersoluble extracts as aforesaid in combination with one or more diluents or excipients which are compatible and pharmaceutically acceptable, and optionally in combination with other drugs such as antibiotics, decongestive agents and vaccines. In such compositions, the watersoluble extracts of the invention are usually present in an amount higher than 0.1% by weight.

The pharmaceutical compositions of the invention may be administerd per oral, rectal or parenteral route or in aerosols. The dosages are a function of the desired effect. They may be between 10 to 50 mg per day for an adult.

The invention will be now further described by the following non limiting examples.

EXAMPLE 1

50 g of delipidated bacterial residues obtained from corynebacterium parvum cells in accordance with the method of A. Aebi et al, Bull. Soc. Chem. Biol. 35, 661 (1953) were ground and homogenized in 250 cm$^3$ water containing 0.1 cm$^3$ detergent "NP-40" using the grinding apparatus of the type "Ultra-Turrax."

After 48 hours stirring at 40° C and centrifugation for 30 minutes at 4° C (4000 rpm), the supernatant layer was heated to 80° C. Ammonium sulfate was then added to obtain a 40% solution. After 12 hours at 4° C and centrifugation for 30 minutes, there was obtained a precipitate called herein after $P_{40}$. Ammonium sulfate was added to the supernatant liquid to produce a 70% solution. After 12 hours at 4° C and centrifugation for 30 minutes, there was obtained a precipitate $P_{70}$ in suspension.

Precipitates $P_{40}$ and $P_{70}$ as well as the last supernatant layer $S_{70}$ were thereafter separately dialyzed against distilled water. The various dialysis solutions were freeze-dried. There was thus-obtained 3.175 g of fraction $P_{40}$, 0.750 g of fraction $P_{70}$ and 1.380 g of fraction $S_{70}$ constituting the raw watersoluble extract.

EXAMPLE 2

Fraction $S_{70}$ obtained in accordance with example 1 was purified by column chromatography on DEAE-cellulose (height: 92 cm; diameter 2.5 cm) equilibrated with a veronal buffer 0.05 M at pH 7 by eluting with a sodium citrate buffer 0.05 M at pH 3 and fractions of 2.3 cm$^3$ were collected and consecutively numbered from 1 to 500, the elution being followed by an optical reading of eluates by means of a spectrophotometer at 280 and 220 nm. Fractions No. 150 to 220 were united; they contained, as shown by the analysis results hereunder, tetrasaccharide-heptapeptide in association with non aminated reducing sugars. After freeze-drying there was obtained 0.125 g of a watersoluble extract having the following characteristics:

appearance: pulverulent white powder-composition:
a. aminoacids
  (molecular ratio); alanine (3), glutamic acid (2), diaminopimelic acid (DAP) (2), aspartic acid (2), glycine (2).
b. amino sugars
  (molecular ratio): N-acetyl-muramic acid (2), N-acetylglucosamine (2).
— molecular weight (calculated on the basis of 3 alanine residues per mole): 4,000 ± 200.
— the contents of aminoacids was 21 ± 4% and of aminosugars was 24.5 ± 3%; the balance being non aminated reducing agents; accordingly by the proportion of DAP is 9.5 ± 1%.

It is to be understood that the foregoing disclosure has been given merely by way of an explanation and without limitation of the general scope of the invention as defined by the appended claims.

We claim:

1. An immunological adjuvant composition comprising low molecular weight hydrosoluble fragments consisting essentially of a disaccharide-tetrapeptide, a tetrasaccharide-heptapeptide and the dimer, trimer and tetramer of the latter, said adjuvant being produced by the steps of subjecting delipidated bacterial residue of Corynebacterium Parvum containing diaminopimelic acid to grinding and homogenization in aqueous medium, centrifuging to remove undissolved solids from the aqueous medium, salting out of active material from the aqueous medium, and dialyzing said fragments containing diaminopimelic acid, having a molecular weight between 1,000 ± 200 and 8,000 ± 200 and being associated with non-aminated reducing sugars.

2. A composition according to claim 1, wherein the homogenization is effected in the presence of a non-ionic detergent.

3. A composition according to claim 1, wherein salting out is effected with ammonium sulfate.

4. A composition according to claim 1, wherein the process of production includes a purification by chromatography.

5. A composition according to claim 4, wherein chromatography is effected on cellulose.

6. A composition according to claim 1, wherein the process of production includes a filtration on a polyacrylamide gel.

7. A composition according to claim 1, wherein the process of production includes lyophilization.

* * * * *